United States Patent [19]

Köster

[11] Patent Number: 5,605,798
[45] Date of Patent: Feb. 25, 1997

[54] DNA DIAGNOSTIC BASED ON MASS SPECTROMETRY

[75] Inventor: Hubert Köster, Concord, Mass.

[73] Assignee: Sequenom, Inc., Boston, Mass.

[21] Appl. No.: 406,199

[22] Filed: Mar. 17, 1995

Related U.S. Application Data

[63] Continuation-in-part of Ser. No. 178,216, Jan. 6, 1994, Pat. No. 5,547,835, which is a continuation-in-part of Ser. No. 1,323, Jan. 7, 1993, abandoned.

[51] Int. Cl.$^6$ .......................... C07H 21/04; C12P 19/34; C12Q 1/68
[52] U.S. Cl. ............................ 435/6; 435/91.1; 435/91.2; 536/25.3; 536/25.4; 935/77; 935/78
[58] Field of Search ........................... 435/6, 91.1, 91.2; 935/77, 78; 536/25.3, 25.4

[56] References Cited

U.S. PATENT DOCUMENTS

| | | | |
|---|---|---|---|
| 4,683,195 | 7/1987 | Mullis et al. | 435/6 |
| 5,003,059 | 3/1991 | Brennan | 536/27 |
| 5,045,694 | 9/1991 | Beavis et al. | 250/287 |
| 5,064,754 | 11/1991 | Mills | 435/6 |
| 5,135,870 | 8/1992 | Williams et al. | 436/86 |
| 5,149,625 | 9/1992 | Church et al. | 435/6 |
| 5,288,644 | 2/1994 | Beavis et al. | 436/94 |

FOREIGN PATENT DOCUMENTS

| | | | |
|---|---|---|---|
| 0360677A1 | 3/1990 | European Pat. Off. | C12Q 1/68 |
| WO89/09282 | 10/1989 | WIPO | C12Q 1/68 |
| WO89/12694 | 12/1989 | WIPO | C12Q 1/68 |
| WO90/14148 | 11/1990 | WIPO | B01D 59/44 |
| WO92/13629 | 8/1992 | WIPO | B01D 59/44 |

OTHER PUBLICATIONS

Ganem et al. Tetrahedron Letters, 34(9):1445–1448, 1993.
Matthews et al. Analytical Biochem. 169:1–25, 1988.
A. Overberg et al. "Laser Desorption Mass Spectrometry. Part II Performance and Applications of Matrix–Assisted Laser Desorption/Ionization of Large Biomolecules" *Mass Spectrometry in the Biological Sciences: A Tutorial.* Editor: M. L. Gross, Kluwer Publications, The Netherlands, (1992) pp. 181–197.

(List continued on next page.)

*Primary Examiner*—W. Gary Jones
*Assistant Examiner*—Paul B. Tran
*Attorney, Agent, or Firm*—Lahive & Cockfield; Beth E. Arnold, Esq.; Giulio A. DeConti, Jr.

[57] ABSTRACT

The invention provides fast and highly accurate mass spectrometer based processes for detecting a particular nucleic acid sequence in a biological sample. Depending on the sequence to be detected, the processes can be used, for example, to diagnose (e.g. prenatally or postnatally) a genetic disease or chromosomal abnormality; a predisposition to a disease or condition (e.g. obesity, artherosclerosis, cancer), or infection by a pathogenic organism (e.g. virus, bacteria, parasite or fungus).

45 Claims, 13 Drawing Sheets

OTHER PUBLICATIONS

B. Barrell, "DNA Sequencing: Present Limitations and Prospects for the Future", *FASEB Journal*, (1991) vol. 5, pp. 40–45.

Bernard A. Connolly, "Oligonucleotides Containing Modified Bases", *Oligonucleotides and Analogues, A Practical Approach*, Edited by F. Eckstein, Oxford University Press (1991), Ch. 7, pp. 155–183.

K. B. Jacobson et al. "Applications of Mass Spectrometry to DNA Sequencing", *GATA*, (1991) 8(8) pp. 223–229.

Hubert Köster et al., "Oligonucleotide Synthesis and Multiplex DNA Sequencing using Chemiluminescent Detection", *Nucleic Acids Research*, Symposium Series No. 24 (1991) pp. 318–321.

George L. Trainor, "DNA Sequencing, Automation and the Human Genome", *Anal. Chem.*, (1990) vol. 62, pp. 418–426.

F. Hillencamp et al., "Matrix Assisted UV–Laser Desorption/Ionization: A New Approach to Mass Spectrometry of Large Biomolecules" *Biological Mass Spectrometry*, Editors: A. L. Burlingame and J. A. McCloskey, Elsevier Science Publishers, B. V., Amsterdam (1989), pp. 49–61.

R. W. Nelson et al., "Volatilization of High Molecular Weight DNA by Pulsed Laser Ablation of Frozen Aqueous Solutions" *Science* (1989) vol. 246, pp. 1585–1887.

Stefan Stahl et al., "Solid Phase DNA Sequencing using the Biotin–Avidin System", *Nucleic Acids Research*, vol. 16, No. 7 (1988) pp. 3025–3039.

Saeko Mizusawa et al., "Improvement of the Dideoxy Chain Termination Method of DNA Sequencing by use of Deoxy-7-Deazaguanosine Triphosphate in Place of dGTP", *Nucleic Acids Research*, vol. 14, No. 3 (1986) pp. 1319–1325.

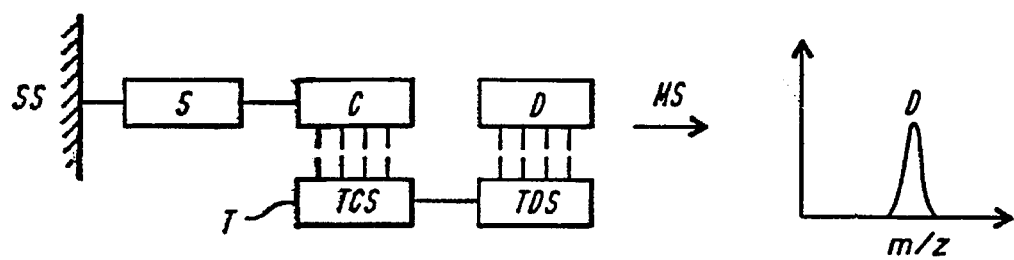
FIG. 1A
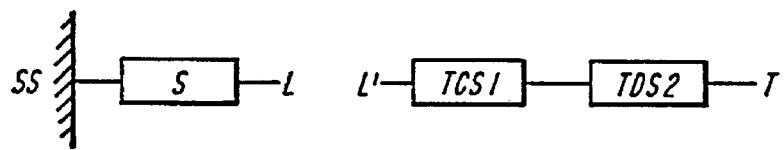
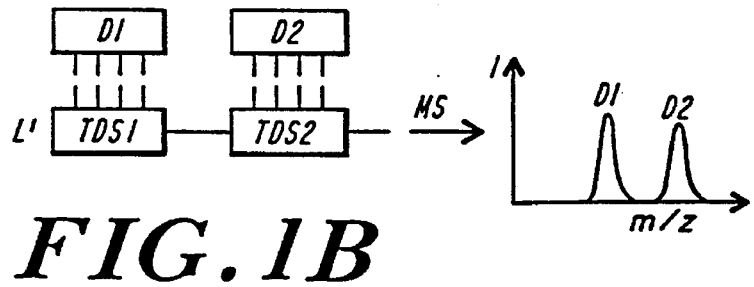
FIG. 1B
FIG. 1C

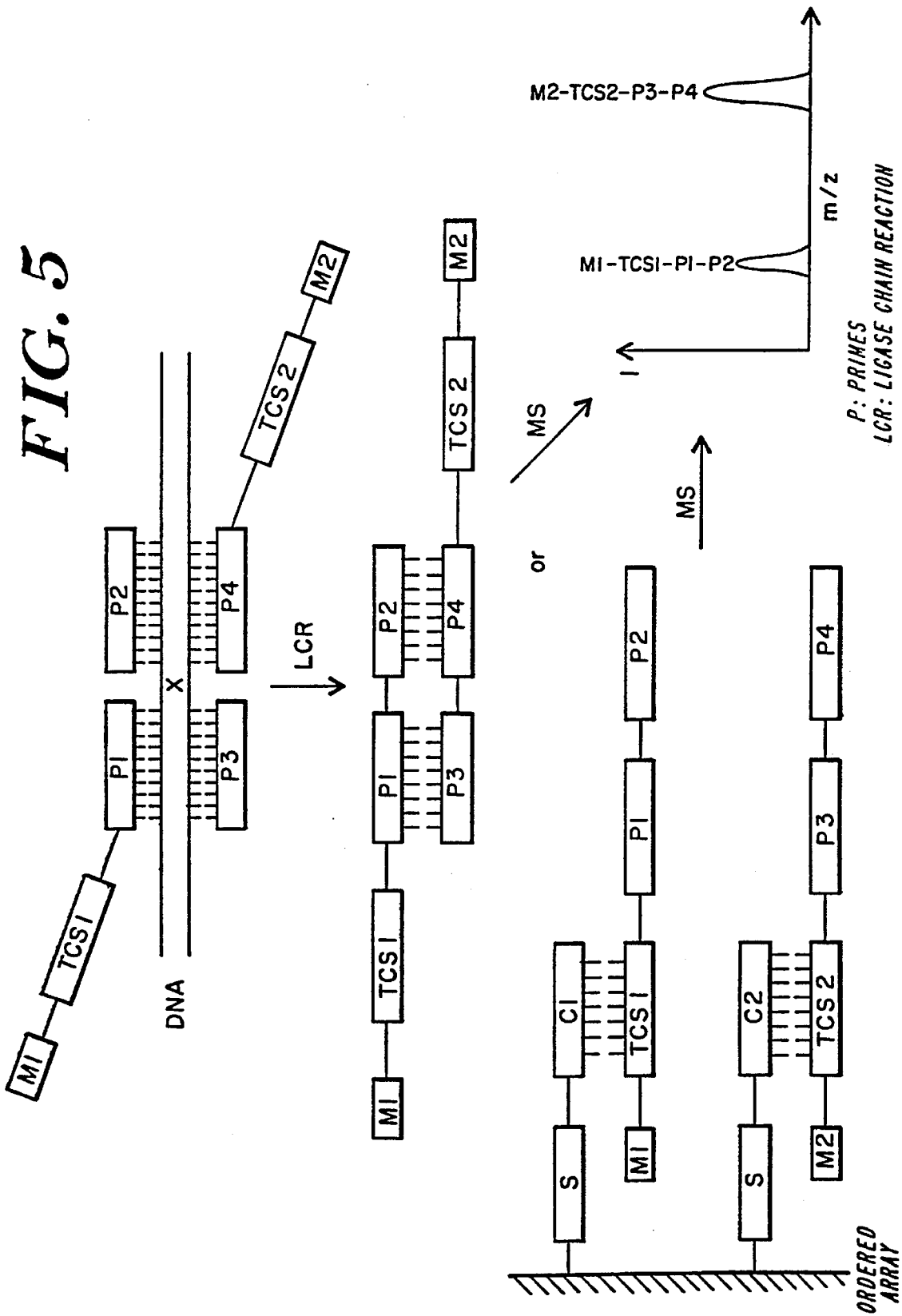

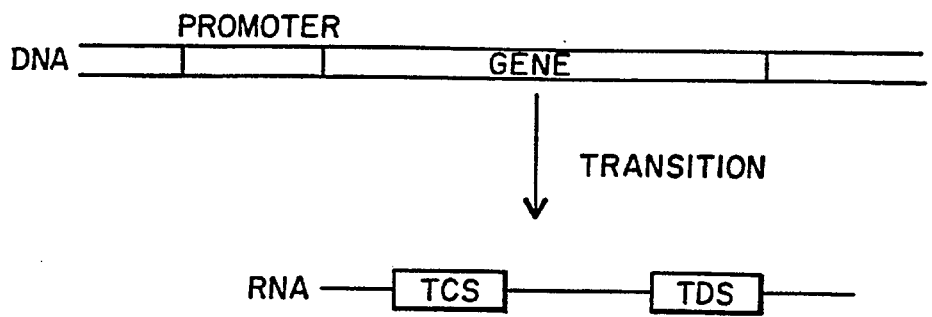
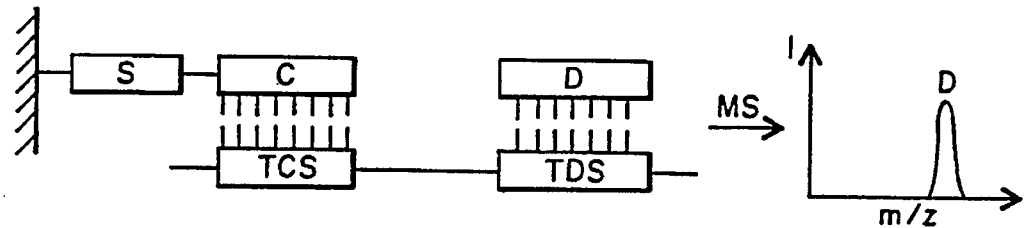
*FIG. 6A*
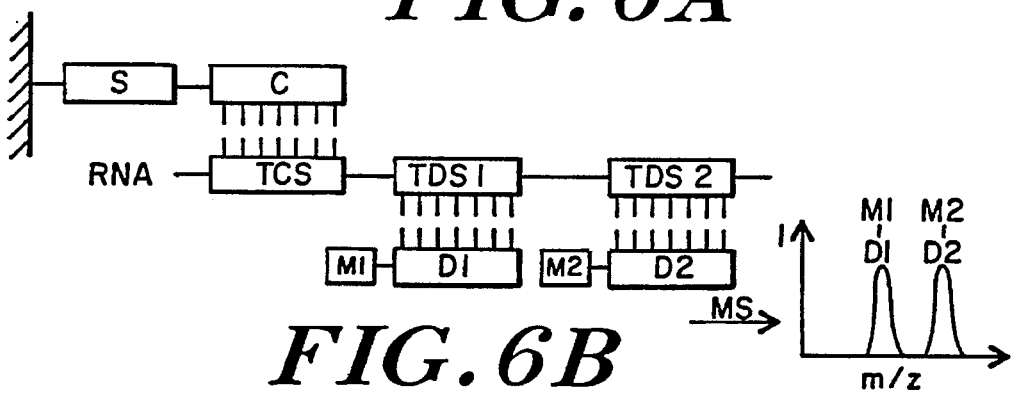
*FIG. 6B*
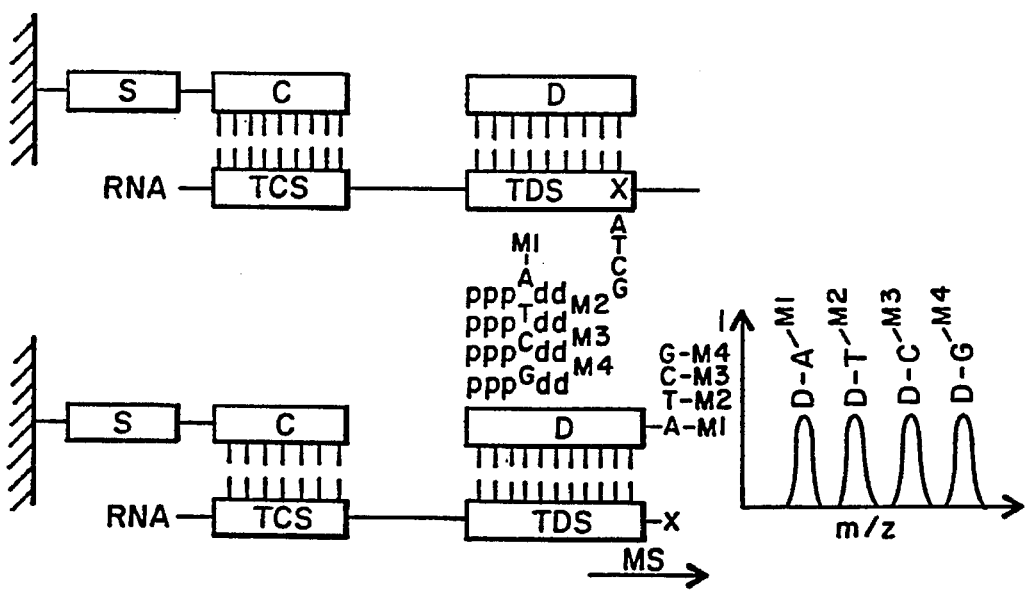
*FIG. 6C*

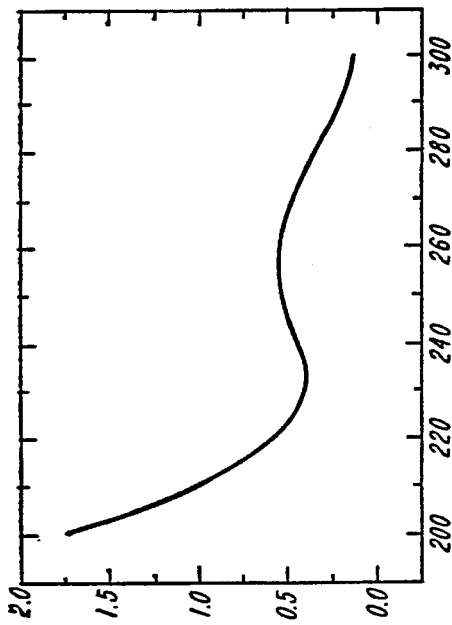
FIG. 9A (i)
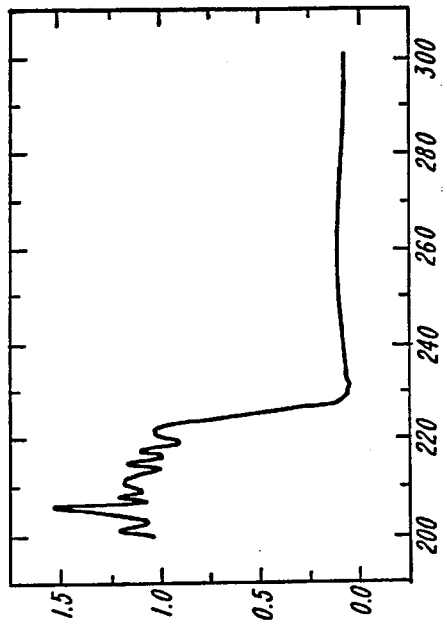
FIG. 9A (ii)
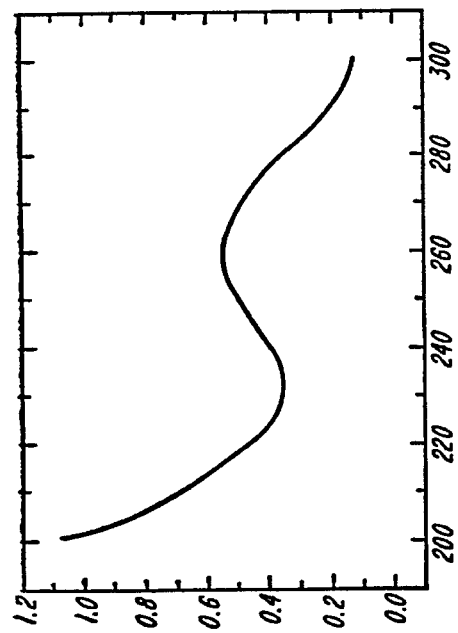
FIG. 9A (iii)
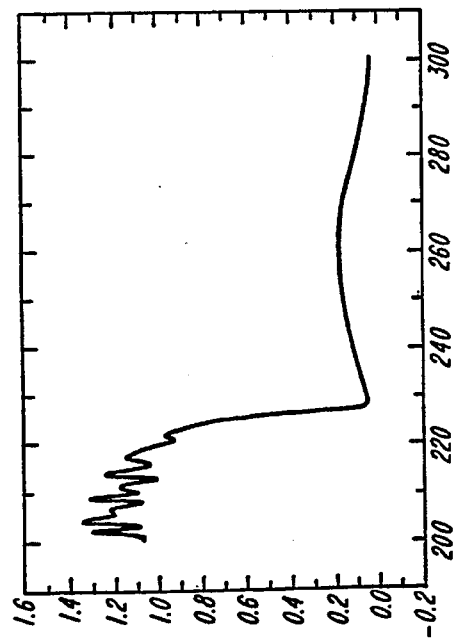
FIG. 9A (iiii)

DNA DIAGNOSTIC BASED ON MASS SPECTROMETRY

RELATED APPLICATIONS

This application is a continuation-in-part of U.S. patent application Ser. No. 08/178,216 filed Jan. 6, 1994, now U.S. Pat. No. 5,547,835 which itself is a continuation-in-part of U.S. patent application Ser. No. 08/001,323 filed Jan. 7, 1993, (now abandoned). The contents of both patent applications are hereby incorporated by reference.

BACKGROUND OF THE INVENTION

The genetic information of all living organisms (e.g. animals, plants and microorganisms) is encoded in deoxyribonucleic acid (DNA). In humans, the complete genome is comprised of about 100,000 genes located on 24 chromosomes (The Human Genome, T. Strachan, BIOS Scientific Publishers, 1992). Each gene codes for a specific protein which after its expression via transcription and translation, fulfills a specific biochemical function within a living cell. Changes in a DNA sequence are known as mutations and can result in proteins with altered or in some cases even lost biochemical activities; this in turn can cause genetic disease. Mutations include nucleotide deletions, insertions or alterations (i.e. point mutations). Point mutations can be either "missense", resulting in a change in the amino acid sequence of a protein or "nonsense" coding for a stop codon and thereby leading to a truncated protein.

More than 3000 genetic diseases are currently known (Human Genome Mutations, D. N. Cooper and M. Krawczak, BIOS Publishers, 1993), including hemophilias, thalassemias, Duchemne Muscular Dystrophy (DMD), Huntington's Disease (HD), Alzheimer's Disease and Cystic Fibrosis (CF). In addition to mutated genes, which result in genetic disease, certain birth defects are the result of chromosomal abnormalities such as Trisomy 21 (Down's Syndrome), Trisomy 13 (Patau Syndrome), Trisomy 18 (Edward's Syndrome), Monosomy X (Turner's Syndrome) and other sex chromosome aneuploidies such as Klienfelter's Syndrome (XXY). Further, there is growing evidence that certain DNA sequences may predispose an individual to any of a number of diseases such as diabetes, arteriosclerosis, obesity, various autoimmune diseases and cancer (e.g. colorectal, breast, ovarian, lung). Viruses, bacteria, fungi and other infectious organisms contain distinct nucleic acid sequences, which are different from the sequences contained in the host cell. Therefore, infectious organisms can also be detected and identified based on their specific DNA sequences.

Since the sequence of 17 nucleotides is specific on statistical grounds, relatively short nucleic acid sequences can be used to detect normal and defective genes in higher organisms and to detect infectious microorganisms (e.g. bacteria, fungi, protists and yeast) and viruses. DNA sequences can even serve as a fingerprint for detection of different individuals within the same species. (Thompson, J. S. and M. W. Thompson, eds., *Genetics in Medicine*, W. B. Saunders Co., Philadelphia, Pa. (1986).

Several methods for detecting DNA are currently being used. For example, nucleic acid sequences can be identified by comparing the mobility of an amplified nucleic acid fragment with a known standard by gel electrophoresis, or by hybridization with a probe, which is complementary to the sequence to be identified. Identification, however, can only be accomplished if the nucleic acid fragment is labeled with a sensitive reporter function (e.g. radioactive ($^{32}$P, $^{35}$S), fluorescent or chemiluminescent). However, radioactive labels can be hazardous and the signals they produce decay over time. Non-isotopic labels (e.g. fluorescent) suffer from a lack of sensitivity and fading of the signal when high intensity lasers are being used. Additionally, performing labeling, electrophoresis and subsequent detection are laborious, time-consuming and error-prone procedures. Electrophoresis is particularly error-prone, since the size or the molecular weight of the nucleic acid cannot be directly correlated to the mobility in the gel matrix. It is known that sequence specific effects, secondary structures and interactions with the gel matrix are causing artefacts.

In general, mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). In the range of molecules with low molecular weight, mass spectrometry has long been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented forming secondary ions by the so-called collision induced dissociation (CID). The fragmentation pattern/pathway very often allows the derivation of detailed structural information. Many applications of mass spectrometric methods are known in the art, particularly in biosciences, and can be found summarized in *Methods in Enzymology*, Vol. 193: "Mass Spectrometry" (J. A. McCloskey, editor), 1990, Academic Press, New York.

Due to the apparent analytical advantages of mass spectrometry in providing high detection sensitivity, accuracy of mass measurements, detailed structural information by CID in conjunction with an MS/MS configuration and speed, as well as on-line data transfer to a computer, there has been considerable interest in the use of mass spectrometry for the structural analysis of nucleic acids. Recent reviews summarizing this field include K. H. Schram, "Mass Spectrometry of Nucleic Acid Components, Biomedical Applications of Mass Spectrometry" 34, 203–287 (1990); and P. F. Crain, "Mass Spectrometric Techniques in Nucleic Acid Research," *Mass Spectrometry Reviews* 9, 505–554 (1990).

However, nucleic acids are very polar biopolymers that are very difficult to volatilize. Consequently, mass spectrometric detection has been limited to low molecular weight synthetic oligonucleotides by determining the mass of the parent molecular ion and through this, confirming the already known oligonucleotide sequence, or alternatively, confirming the known sequence through the generation of secondary ions (fragment ions) via CID in an MS/MS configuration utilizing, in particular, for the ionization and volatilization, the method of fast atomic bombardment (FAB mass spectrometry) or plasma desorption (PD mass spectrometry). As an example, the application of FAB to the analysis of protected dimeric blocks for chemical synthesis of oligodeoxynucleotides has been described (Köster et al. *Biomedical Environmental Mass Spectrometry* 14, 111–116 (1987)).

Two more recent ionization/desorption techniques are electrospray/ionspray (ES) and matrix-assisted laser desorption/ionization (MALDI). ES mass spectrometry has been introduced by Fenn et al. (*J. Phys. Chem.* 88, 4451–59 (1984); PCT Application No. WO 90/14148) and current applications are summarized in recent review articles (R. D.

Smith et al., *Anal. Chem.* 62, 882–89 (1990) and B. Ardrey, Electrospray Mass Spectrometry, *Spectroscopy Europe*, 4, 10–18 (1992)). The molecular weights of a tetradecanucleotide (Covey et al. "The Determination of Protein, Oligonucleotide and Peptide Molecular Weights by Ionspray Mass Spectrometry," *Rapid Communications in Mass Spectrometry*, 2, 249–256 (1988)), and of a 21-mer (*Methods in Enzymology*, 193, "Mass Spectrometry" (McCloskey, editor), p. 425, 1990, Academic Press, New York) have been published. As a mass analyzer, a quadrupole is most frequently used. The determination of molecular weights in femtomole amounts of sample is very accurate due to the presence of multiple ion peaks which all could be used for the mass calculation.

MALDI mass spectrometry, in contrast, can be particularly attractive when a time-of-flight (TOF) configuration is used as a mass analyzer. The MALDI-TOF mass spectrometry has been introduced by Hillenkamp et al. ("Matrix Assisted UV-Laser Desorption/Ionization: A New Approach to Mass Spectrometry of Large Biomolecules," *Biological Mass Spectrometry* (Burlingame and McCloskey, editors), Elsevier Science Publishers, Amsterdam, pp. 49–60, 1990.) Since, in most cases, no multiple molecular ion peaks are produced with this technique, the mass spectra, in principle, look simpler compared to ES mass spectrometry.

Although DNA molecules up to a molecular weight of 410,000 daltons have been desorbed and volatilized (Williams et al., "Volatilization of High Molecular Weight DNA by Pulsed Laser Ablation of Frozen Aqueous Solutions," *Science*, 246, 1585–87 (1989)), this technique has so far only shown very low resolution (oligothymidylic acids up to 18 nucleotides, Huth-Fehre et al., *Rapid Communications in Mass Spectrometry*, 6, 209–13 (1992); DNA fragments up to 500 nucleotides in length K. Tang et al., *Rapid Communications in Mass Spectrometry*, 8, 727–730 (1994); and a double-stranded DNA of 28 base pairs (Williams et al., "Time-of-Flight Mass Spectrometry of Nucleic Acids by Laser Ablation and Ionization from a Frozen Aqueous Matrix," *Rapid Communications in Mass Spectrometry*, 4, 348–351 (1990)).

Japanese Patent No. 59-131909 describes an instrument, which detects nucleic acid fragments separated either by electrophoresis, liquid chromatography or high speed gel filtration. Mass spectrometric detection is achieved by incorporating into the nucleic acids, atoms which normally do not occur in DNA such as S, Br, I or Ag, Au, Pt, Os, Hg.

SUMMARY OF THE INVENTION

The instant invention provides mass spectrometric processes for detecting a particular nucleic acid sequence in a biological sample. Depending on the sequence to be detected, the processes can be used, for example, to diagnose (e.g. prenatally or postnatally) a genetic disease or chromosomal abnormality; a predisposition to a disease or condition (e.g. obesity, artherosclerosis, cancer), or infection by a pathogenic organism (e.g. virus, bacteria, parasite or fungus).

In one embodiment, a nucleic acid molecule containing the nucleic acid sequence to be detected (i.e. the target) is initially immobilized to a solid support. Immobilization can be accomplished, for example, based on hybridization between a portion of the target nucleic acid molecule, which is distinct from the target detection site and a capture nucleic acid molecule, which has been previously immobilized to a solid support. Alternatively, immobilization can be accomplished by direct bonding of the target nucleic acid molecule and the solid support. Preferably, there is a spacer (e.g. a nucleic acid molecule) between the target nucleic acid molecule and the support. A detector nucleic acid molecule (e.g. an oligonucleotide or oligonucleotide mimetic), which is complementary to the target detection site can then be contacted with the target detection site and formation of a duplex, indicating the presence of the target detection site can be detected by mass spectrometry. In preferred embodiments, the target detection site is amplified prior to detection and the nucleic acid molecules are conditioned. In a further preferred embodiment, the target detection sequences are arranged in a format that allows multiple simultaneous detections (multiplexing).

In another embodiment, immobilization of the target nucleic acid molecule is an optional rather than a required step. Instead, once a nucleic acid molecule has been obtain from a biological sample, the target detection sequence is amplified and directly detected by mass spectrometry. In preferred embodiments, the target detection site and/or the detector oligonucleotides are conditioned prior to mass spectrometric detection. In another preferred embodiment, the amplified target detection sites are arranged in a format that allows multiple simultaneous detections (multiplexing).

In a further embodiment, nucleic acid molecules which have been transcribed from nucleic acid obtained from a biological sample can be specifically digested using one or more nucleases (using deoxyribonucleases for DNA or ribonucleases for RNA) and the fragments captured on a solid support carrying the corresponding complementary sequences. Hybridization events and the actual molecular weights of the captured target sequences provide information on whether and where mutations in the gene are present. The array can be analyzed spot by spot using mass spectrometry. DNA can be similarly digested using a cocktail of nucleases including restriction endonucleases. In a preferred embodiment, the nucleic acid fragments are conditioned prior to mass spectrometric detection.

The processes of the invention provide for increased accuracy and reliability of nucleic acid detection by mass spectrometry. In addition, the processes allow for rigorous controls to prevent false negative or positive results. The processes of the invention avoids electrophoretic steps; labeling and subsequent detection of a label. In fact it is estimated that the entire procedure, including nucleic acid isolation, amplification, and mass spec analysis requires only about 2–3 hours time. Therefore the instant disclosed processes of the invention are faster and less expensive to perform than existing DNA detection systems. In addition, because the instant disclosed processes allow the nucleic acid fragments to be identified and detected at the same time by their specific molecular weights (an unambiguous physical standard), the disclosed processes are also much more accurate and reliable than currently available procedures.

BRIEF DESCRIPTION OF THE FIGURES

FIG. 1A is a diagram showing a process for performing mass spectrometric analysis on one target detection site (TDS) contained within a target nucleic acid molecule (T), which has been obtained from a biological sample. A specific capture sequence (C) is attached to a solid support (SS) via a spacer (S). The capture sequence is chosen to specifically hybridize with a complementary sequence on the target nucleic acid molecule (T), known as the target capture site (TCS). The spacer (S) faciliates unhindered hybridization. A detector nucleic acid sequence (D), which is complementary to the TDS is then contacted with the TDS. Hybridization between D and the TDS can be detected by mass spectrometry.

FIG. 1B is a diagram showing a process for performing mass spectrometric analysis on at least one target detection site (here TDS 1 and TDS 2) via direct linkage to a solid support. The target sequence (T) containing the target detection site (TDS 1 and TDS 2) is immobilized to a solid support via the formation of a reversible or irreversible bond formed between an appropriate functionality (L') on the target nucleic acid molecule (T) and an appropriate functionality (L) on the solid support. Detector nucleic acid sequences (here D1 and D2), which are complementary to a target detection site (TDS 1 or TDS 2) are then contacted with the TDS. Hybridization between TDS 1 and D1 and/or TDS 2 and D2 can be detected and distinguished based on molecular weight differences.

FIG. 1C is a diagram showing a process for detecting a wildtype ($D^{wt}$) and/or a mutant ($D^{mut}$) sequence in a target (T) nucleic acid molecule. As in FIG. 1A, a specific capture sequence (C) is attached to a solid support (A) via a spacer (S). In addition, the capture sequence is chosen to specifically interact with a complementary sequence on the target sequence (T), the target capture site (TCS) to be detected through hybridization. However, if the target detection site (TDS) includes a mutation, X, which changes the molecular weight, mutated target detection sites can be distinguished from wildtype by mass spectrometry. Preferably, the detector nucleic acid molecule (D) is designed so that the mutation is in the middle of the molecule and therefore would not lead to a stable hybrid if the wildtype detector oligonucleotide ($D^{wt}$) is contacted with the target detector sequence, e.g. as a control. The mutation can also be detected if the mutated detector oligonucleotide ($D^{mut}$) with the matching base at the mutated position is used for hybridization. If a nucleic acid molecule obtained from a biological sample is heterozygous for the particular sequence (i.e. contain both $D^{wt}$ and $D^{mut}$), both $D^{wt}$ and $D^{mut}$ will be bound to the appropriate strand and the mass difference allows both $D^{wt}$ and $D^{mut}$ to be detected simultaneously.

FIG. 5 is a diagram showing how amplification (here ligase chain reaction (LCR)) products can be prepared and detected by mass spectrometry. Mass differentiation can be achieved by the mass modifying functionalities (M1 and M2) attached to primers (P1 and P4 respectively). Detection by mass spectrometry can be accomplished directly (i.e. without employing immobilization and target capturing sites (TCS)). Multiple LCR reactions can be performed in parallel by providing an ordered array of capturing sequences (C). This format allows separation of the ligation products and spot by spot identification via mass spectrometry or multiplexing if mass differentiation is sufficient.

FIG. 6A is a diagram showing mass spectrometric analysis of a nucleic acid molecule, which has been amplified by a transcription amplification procedure. An RNA sequence is captured via its TCS sequence, so that wildtype and mutated target detection sites can be detected as above by employing appropriate detector oligonucleotides (D).

FIG. 6B is a diagram showing multiplexing to detect two different (mutated) sites on the same RNA in a simultaneous fashion using mass-modified detector oligonucleotides M1–D1 and M2–D2.

FIG. 6C is a diagram of a different multiplexing procedure for detection of specific mutations by employing mass modified dideoxynucleoside triphosphates and an RNA dependent DNA polymerase. Alternatively, DNA dependent polymerase and ribonucleotide phosphates can be employed. This format allows for simultaneous detection of all four base possibilities at the site of a mutation (X).

FIG. 9A shows a spectra resulting from the experiment described in the following Example 1. Panel i) shows the absorbance of the 26-mer before hybridization. Panel ii) shows the filtrate of the centrifugation after hybridization. Panel iii) shows the results after the first wash with 50 mM ammonium citrate. Panel iv) shows the results after the second wash with 50 mM ammonium citrate.

DETAILED DESCRIPTION OF THE INVENTION

Figure 2:
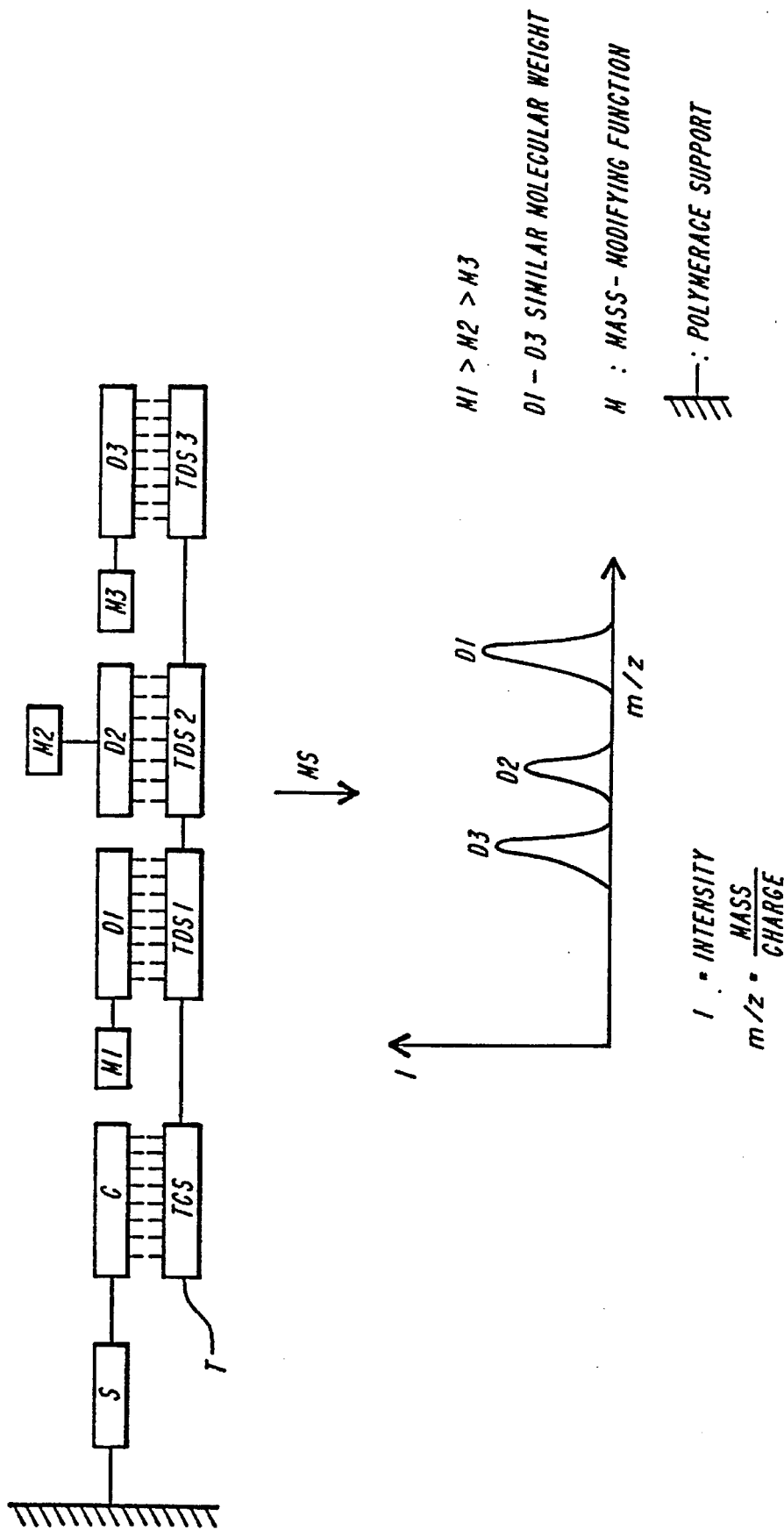
FIG. 2 is a diagram showing a process in which several mutations are simultaneously detected on one target sequence by employing corresponding detector oligonucleotides. The molecular weight differences between the detector oligonucleotides D1, D2 and D3 must be large enough so that simultaneous detection (multiplexing) is possible. This can be achieved either by the sequence itself (composition or length) or by the introduction of mass-modifying functionalities M1–M3 into the detector oligonucleotide.

In general, the instant invention provides mass spectrometric processes for detecting a particular nucleic acid sequence in a biological sample. As used herein, the term "biological sample" refers to any material obtained from any living source (e.g. human, animal, plant, bacteria, fungi, protist, virus). For use in the invention, the biological sample should contain a nucleic acid molecule. Examples of appropriate biological samples for use in the instant invention include: solid materials (e.g. tissue, cell pellets, biopsies) and biological fluids (e.g. urine, blood, saliva, amniotic fluid).

Nucleic acid molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Rolff, A. et al. PCR: Clinical Diagnostics and Research, Springer (1994)).

To obtain an appropriate quantity of a nucleic acid molecules on which to perform mass spectrometry, amplification may be necessary. Examples of appropriate amplification procedures for use in the invention include: cloning (Sambrook et al., Molecular Cloning: A Laboratory Manual, Cold Spring Harbor Laboratory Press, 1989), polymerase chain reaction (PCR) (C. R. Newton and A. Graham, PCR, BIOS Publishers, 1994), ligase chain reaction (LCR) (F. Barany *Proc. Natl. Acad. Sci USA* 88, 189–93 (1991), strand displacement amplification (SDA) (G. Terrance Walker et al., *Nucleic Acids Res.* 22, 2670–77 (1994)) and variations such as RT-PCR, allele-specific amplification (ASA) etc.

To facilitate mass spectrometric analysis, a nucleic acid molecule containing a nucleic acid sequence to be detected can be immobilized to a solid support. Examples of appropriate solid supports include beads (e.g. silica gel, controlled pore glass, magnetic, Sephadex/Sepharose, cellulose), flat surfaces or chips (e.g. capillaries, glass fiber filters, glass surfaces, metal surfaces (steel, gold, silver, aluminum, and copper), plastic (e.g. polyethylene, polypropylene, polyamide, polyvinylidenedifluoride membranes or microtiter plates)); or pins or combs made from similar materials comprising beads or flat surfaces.

Immobilization can be accomplished, for example, based on hybridization between a capture nucleic acid sequence, which has already been immobilized to the support and a complementary nucleic acid sequence, which is also contained within the nucleic acid molecule containing the nucleic acid sequence to be detected (FIG. 1A). So that hybridization between the complementary nucleic acid molecules is not hindered by the support, the capture nucleic acid can include a spacer region of at least about five nucleotides in length between the solid support and the capture nucleic acid sequence. The duplex formed will be cleaved under the influence of the laser pulse and desorption can be initiated. The solid support-bound base sequence can be presented through natural oligoribo- or oligodeoxyribonucleotide as well as analogs (e.g. thio-modified phosphodiester or phosphotriester backbone) or employing oligonucleotide mimetics such as PNA analogs (see e.g. Nielsen et al., *Science,* 254, 1497 (1991)) which render the base sequence less susceptible to enzymatic degradation and hence increases overall stability of the solid support-bound capture base sequence.

Alternatively, a target detection site can be directly linked to a solid support via a reversible or irreversible bond between an appropriate functionality (L') on the target nucleic acid molecule (T) and an appropriate functionality (L) on the capture molecule (FIG. 1B). A reversible linkage can be such that it is cleaved under the conditions of mass spectrometry (i.e., a photocleavable bond such as a charge transfer complex or a labile bond being formed between relatively stable organic radicals). Furthermore, the linkage can be formed with L' being a quaternary ammonium group, in which case, preferably, the surface of the solid support carries negative charges which repel the negatively charged nucleic acid backbone and thus facilitate the desorption required for analysis by a mass spectrometer. Desorption can occur either by the heat created by the laser pulse and/or, depending on L,' by specific absorption of laser energy which is in resonance with the L' chromophore.

By way of example, the L-L' chemistry can be of a type of disulfide bond (chemically cleavable, for example, by mercaptoethanol or dithioerythrol), a biotin/streptavidin system, a heterobifunctional derivative of a trityl ether group (Köster et al., "A Versatile Acid-Labile Linker for Modification of Synthetic Biomolecules," *Tetrahedron Letters* 31, 7095 (1990)) which can be cleaved under mildly acidic conditions as well as under conditions of mass spectrometry, a levulinyl group cleavable under almost neutral conditions with a hydrazinium/acetate buffer, an arginine-arginine or lysine-lysine bond cleavable by an endopeptidase enzyme like trypsin or a pyrophosphate bond cleavable by a pyrophosphatase.

The functionalities, L and L,' can also form a charge transfer complex and thereby form the temporary L-L' linkage. Since in many cases the "charge-transfer band" can be determined by UV/vis spectrometry (see e.g. *Organic Charge Transfer Complexes* by R. Foster, Academic Press, 1969), the laser energy can be tuned to the corresponding energy of the charge-transfer wavelength and, thus, a specific desorption off the solid support can be initiated. Those skilled in the art will recognize that several combinations can serve this purpose and that the donor functionality can be either on the solid support or coupled to the nucleic acid molecule to be detected or vice versa.

In yet another approach, a reversible L-L' linkage can be generated by homolytically forming relatively stable radicals. Under the influence of the laser pulse, desorption (as discussed above) as well as ionization will take place at the radical position. Those skilled in the art will recognize that other organic radicals can be selected and that, in relation to the dissociation energies needed to homolytically cleave the bond between them, a corresponding laser wavelength can be selected (see e.g. *Reactive Molecules* by C. Wentrup, John Wiley & Sons, 1984).

Figure 4:
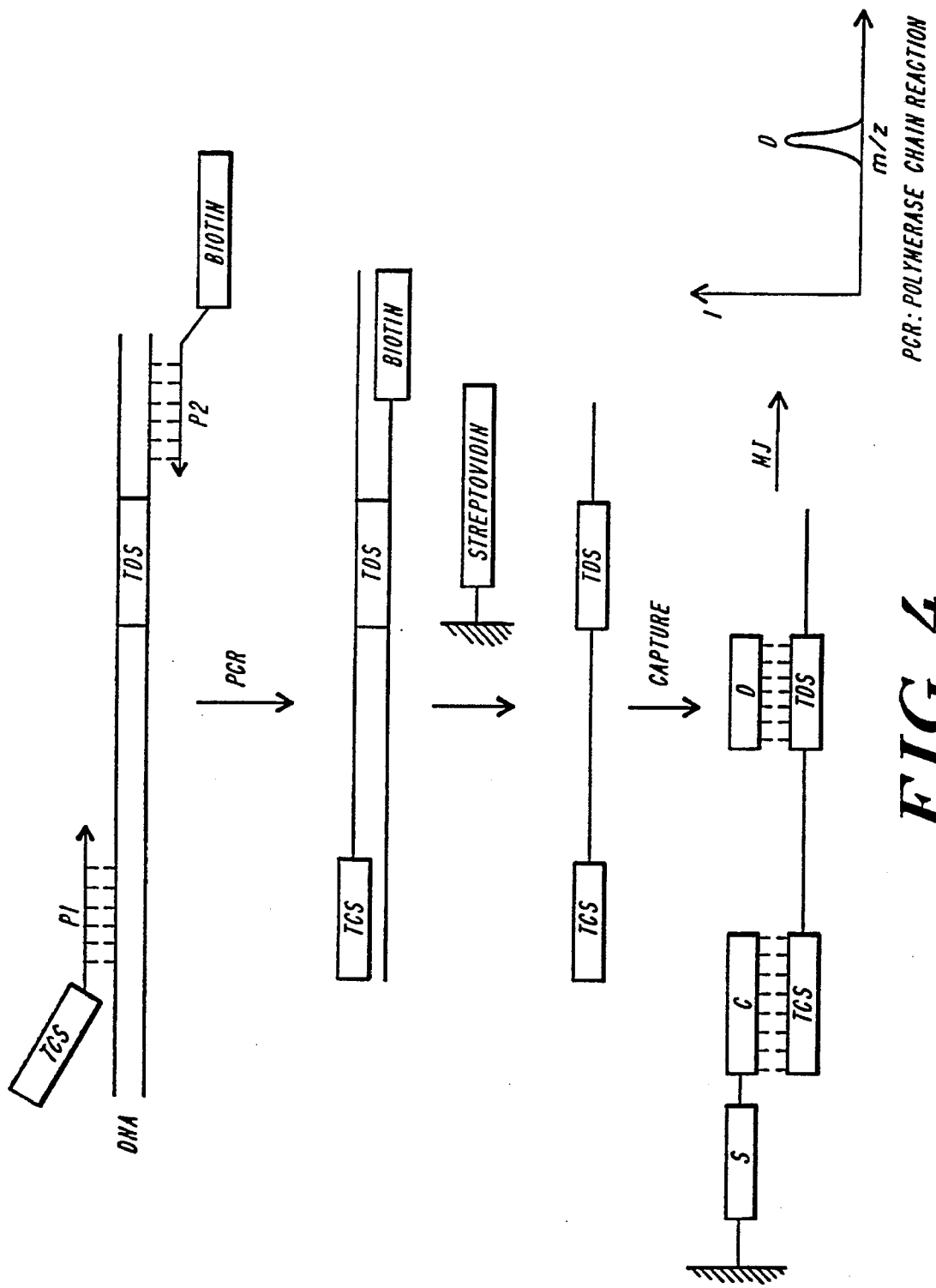
FIG. 4 is a diagram showing a format wherein a predesigned target capture site (TCS) is incorporated into the target sequence using PCR amplification. Only one strand is captured, the other is removed (e.g., based on the interaction between biotin and streptavidin coated magnetic beads). If the biotin is attached to primer 1 the other strand can be appropriately marked by a TCS. Detection is as described above through the interaction of a specific detector oligonucleotide D with the corresponding target detection site TDS via mass spectrometry.
Figure 7:
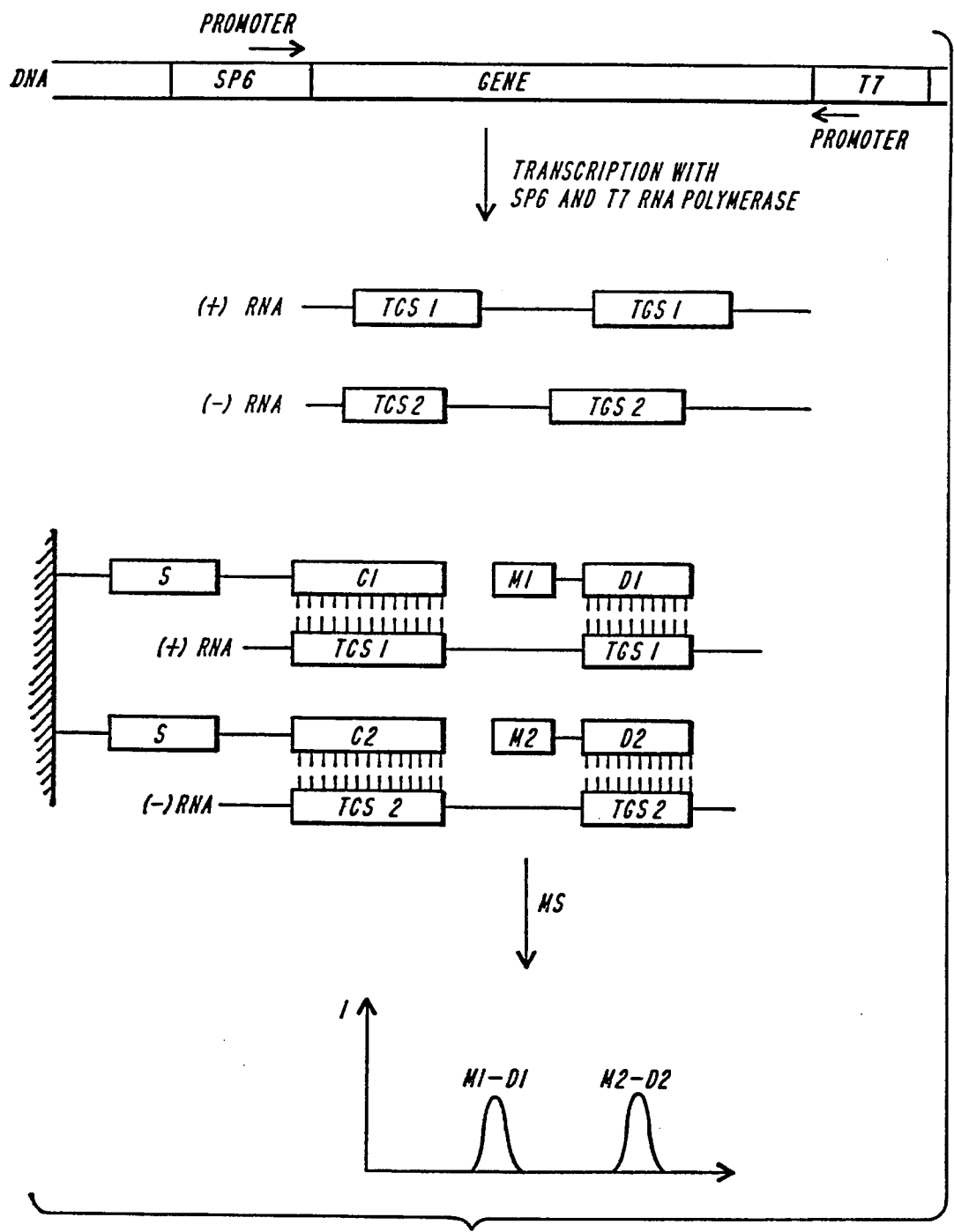
FIG. 7 is a diagram showing how both strands of a target DNA can be prepared for detection using transcription vectors having two different promoters at opposite locations (e.g. the SP6 and the T7 promoter). This format is particularly useful for detecting heterozygous target detection sites (TDS). Employing the SP6 or the T7 RNA polymerase both strands could be transcribed separately or simultaneously. Both RNAs can be specifically captured and simultaneously detected using appropriately mass-differentiated detector oligonucleotides. This can be accomplished either directly in solution or by parallel processing of many target sequences on an ordered array of specifically immobilized capturing sequences.

An anchoring function L' can also be incorporated into a target capturing sequence (TCS) by using appropriate primers during an amplification procedure, such as PCR (FIG. 4), LCR (FIG. 5) or transcription amplification (FIG. 6A).

Prior to mass spectrometric analysis, it may be useful to "condition" nucleic acid molecules, for example to decrease the laser energy required for volatization and/or to minimize fragmentation. Conditioning is preferably performed while a target detection site is immobilized. An example of conditioning is modification of the phosphodiester backbone of the nucleic acid molecule (e.g. cation exchange), which can be useful for eliminating peak broadening due to a heterogeneity in the cations bound per nucleotide unit. Contacting a nucleic acid molecule with an alkylating agent such as akyliodide, iodoacetamide, β-iodoethanol, or 2,3-epoxy-1-propanol, the monothio phosphodiester bonds of a nucleic acid molecule can be transformed into a phosphotriester bond. Further conditioning involves incorporating nucleotides which reduce sensitivity for depurination (fragmentation during MS) such as N7- or N9-deazapurine nucleotides, or RNA building blocks or using oligonucleotide triesters or incorporating phosphorothioate functions which are alkylated or employing oligonucleotide mimetics such as PNA.

For certain applications, it may be useful to simultaneously detect more than one (mutated) loci on a particular captured nucleic acid fragment (on one spot of an array) or it may be useful to perform parallel processing by using oligonucleotide or oligonucleotide mimetic arrays on various solid supports. "Multiplexing" can be achieved by several different methodologies. For example, several mutations can be simultaneously detected on one target sequence by employing corresponding detector molecules (e.g. oligonucleotides or oligonucleotide mimetics. However, the molecular weight differences between the detector oligonucleotides D1, D2 and D3 must be large enough so that simultaneous detection (multiplexing) is possible. This can be achieved either by the sequence itself (composition or length) or by the introduction of mass-modifying functionalities M1–M3 into the detector oligonucleotide.(FIG. 2)

Mass modifying moieties can be rotached, for instance, to either the 5'-end of the oligonucleotide ($M^1$), to the nucleobase (or bases) ($M^2$, $M^7$), to the phosphate backbone ($M^3$), and to the 2'-position of the nucleoside (nucleosides) ($M^4$, $M^6$) or/and to the terminal 3'-position ($M^5$). Examples of mass modifying moieties include, for example, a halogen, an azido, or of the type, XR, wherein X is a linking group and R is a mass-modifying functionality. The mass-modifying functionality can thus be used to introduce defined mass increments into the oligonucleotide molecule.

Here the mass-modifying moiety, M, can be attached either to the nucleobase, $M^2$ (in case of the $c^7$-deazanucleosides also to C-7, $M^7$), to the triphosphate group at the alpha phosphate, $M^3$, or to the 2'-position of the sugar ring of the nucleoside triphosphate, $M^4$ and $M^6$. Furthermore, the mass-modifying functionality can be added so as to affect chain termination, such as by attaching it to the 3'-position of the sugar ring in the nucleoside triphosphate, $M^5$. For those skilled in the art, it is clear that many combinations can serve the purpose of the invention equally well. In the same way, those skilled in the art will recognize that chain-elongating nucleoside triphosphates can also be mass-modified in a similar fashion with numerous variations and combinations in functionality and attachment positions.

Without limiting the scope of the invention, the mass-modification, M, can be introduced for X in XR as well as using oligo-/polyethylene glycol derivatives for R. The mass-modifying increment in this case is 44, i.e. five different mass-modified species can be generated by just changing m from 0 to 4 thus adding mass units of 45 (m=0), 89 (m=1), 133 (m=2), 177 (m=3) and 221 (m=4) to the nucleic acid molecule (e.g. detector oligonucleotide (D) or the nucleoside triphosphates (FIG. 6(C)), respectively). The oligo/polyethylene glycols can also be monoalkylated by a lower alkyl such as methyl, ethyl, propyl, isopropyl, t-butyl and the like. A selection of linking functionalities, X, are also illustrated. Other chemistries can be used in the mass-modified compounds, as for example, those described recently in *Oligonucleotides and Analogues, A Practical Approach,* F. Eckstein, editor, IRL Press, Oxford, 1991.

In yet another embodiment, various mass-modifying functionalities, R, other than oligo/polyethylene glycols, can be selected and attached via appropriate linking chemistries, X. A simple mass-modification can be achieved by substituting H for halogens like F, Cl, Br and/or I, or pseudohalogens such as SCN, NCS, or by using different alkyl, aryl or aralkyl moieties such as methyl, ethyl, propyl, isopropyl, t-butyl, hexyl, phenyl, substituted phenyl, benzyl, or functional groups such as $CH_2F$, $CHF_2$, $CF_3$, $Si(CH_3)_3$, $Si(CH_3)_2(C_2H_5)$, $Si(CH_3)(C_2H_5)_2$, $Si(C_2H_5)_3$. Yet another mass-modification can be obtained by attaching homo- or heteropeptides through the nucleic acid molecule (e.g. detector (D)) or nucleoside triphosphates. One example useful in generating mass-modified species with a mass increment of 57 is the attachment of oligoglycines, e.g., mass-modifications of 74 (r=1, m=0), 131 (r=1, m=2), 188 (r=1, m=3), 245 (r=1, m=4) are achieved. Simple oligoamides also can be used, e.g., mass-modifications of 74 (r=1, m=0), 88 (r=2, m=0), 102 (r=3, m=0), 116(r=4, m=0), etc. are obtainable. For those skilled in the art, it will be obvious that there are numerous possibilities in addition to those mentioned above.

As used herein, the superscript 0-i designates i+1 mass differentiated nucleotides, primers or tags. In some instances, the superscript 0 can designate an unmodified species of a particular reactant, and the superscript i can designate the i-th mass-modified species of that reactant. If, for example, more than one species of nucleic acids are to be concurrently detected, then i+1 different mass-modified detector oligonucleotides ($D^0$, $D^1$, ... $D^i$) can be used to distinguish each species of mass modified detector oligonucleotides (D) from the others by mass spectrometry.

Different mass-modified detector oligonucleotides can be used to simultaneously detect all possible variants/mutants simultaneously (FIG. 6B). Alternatively, all four base permutations at the site of a mutation can be detected by designing and positioning a detector oligonucleotide, so that it serves as a primer for a DNA/RNA polymerase (FIG. 6C). For example, mass modifications can be incorporated during the amplification process.

Figure 3:
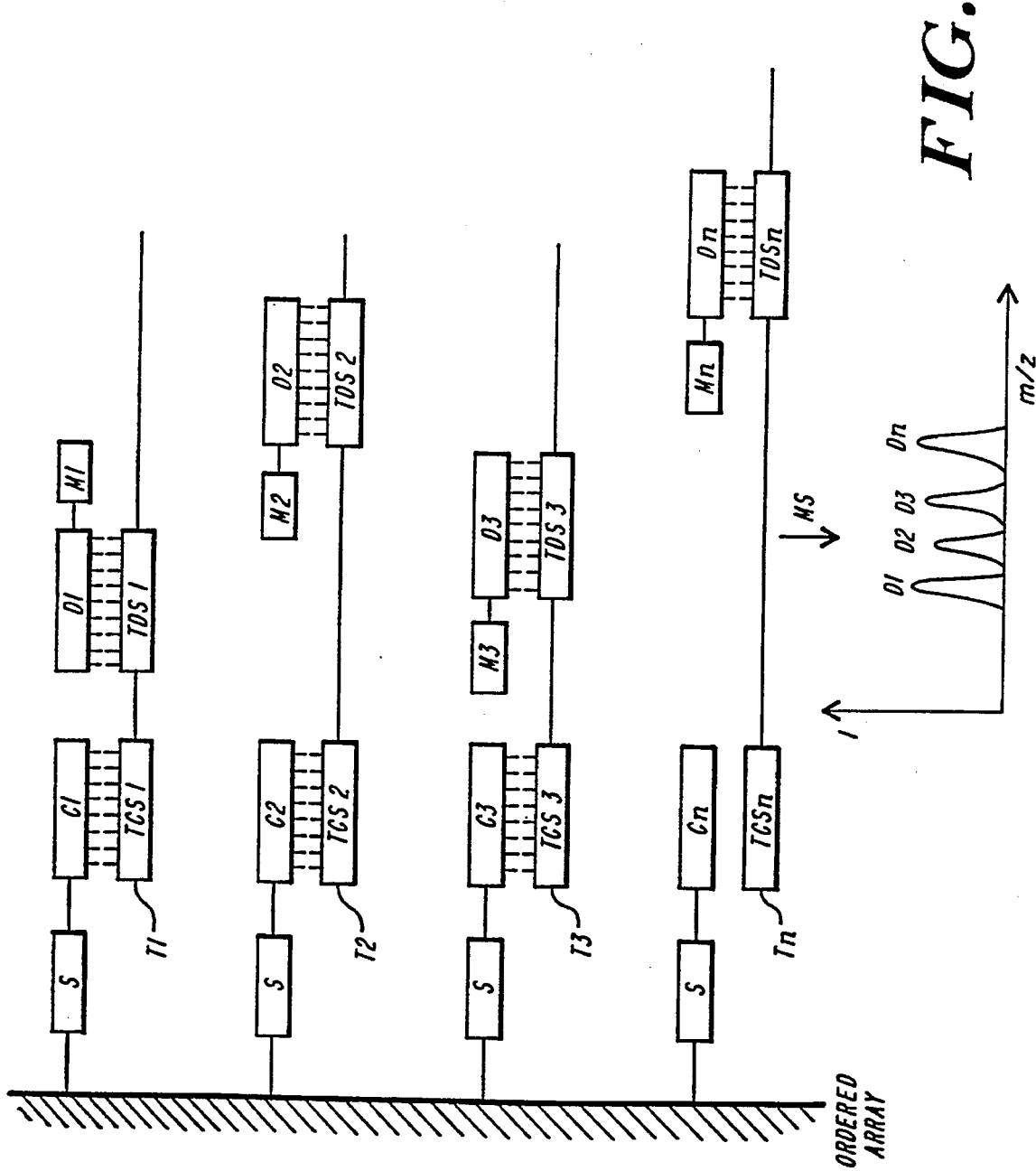
FIG. 3 is a diagram showing still another multiplex detection format. In this embodiment, differentiation is accomplished by employing different specific capture sequences which are position-specifically immobilized on a flat surface (e.g., a 'chip array'). If different target sequences T1–Tn are present, their target capture sites TCS1–TCSn will interact with complementary immobilized capture sequences C1–Cn. Detection is achieved by employing appropriately mass differentiated detector oligonucleotides D1–Dn, which are mass differentiated either by their sequences or by mass modifying functionalities M1–Mn.

FIG. 3 shows a different multiplex detection format, in which differentiation is accomplished by employing different specific capture sequences which are position-specifically immobilized on a flat surface (e.g., a 'chip array'). If different target sequences T1–Tn are present, their target capture sites TCS1–TCSn will specifically interact with complementary immobilized capture sequences C1–Cn. Detection is achieved by employing appropriately mass differentiated detector oligonucleotides D1–Dn, which are mass differentiated either by their sequences or by mass modifying functionalities M1–Mn.

Preferred mass spectrometer formats for use in the invention are matrix assisted laser desorption ionization (MALDI), electrospray (ES), ion cyclotron resonance (ICR) and Fourier Transform. For ES, the samples, dissolved in water or in a volatile buffer, are injected either continuously or discontinuously into an atmospheric pressure ionization interface (API) and then mass analyzed by a quadrupole. The generation of multiple ion peaks which can be obtained using ES mass spectrometry can increase the accuracy of the mass determination. Even more detailed information on the specific structure can be obtained using an MS/MS quadrupole configuration In MALDI mass spectrometry, various mass analyzers can be used, e.g., magnetic sector/magnetic deflection instruments in single or triple quadrupole mode (MS/MS), Fourier transform and time-of-flight (TOF) configurations as is known in the art of mass spectrometry. For the desorption/ionization process, numerous matrix/laser combinations can be used. Ion-trap and reflectron configurations can also be employed.

The mass spectrometric processes described above can be used, for example, to diagnose any of the more than 3000 genetic diseases currently known or to be identified (e.g. hemophilias, thalassemias, Duchenne Muscular Dystrophy (DMD), Huntington's Disease (HD), Alzheimer's Disease and Cystic Fibrosis (CF)).

In addition to mutated genes, which result in genetic disease, certain birth defects are the result of chromosomal abnormalities such as Trisomy 21 (Down's Syndrome), Trisomy 13 (Patau Syndrome), Trisomy 18 (Edward's Syndrome), Monosomy X (Turner's Syndrome) and other sex chromosome aneuploidies such as Klienfelter's Syndrome (XXY).

Further, there is growing evidence that certain DNA sequences may predispose an individual to any of a number of diseases such as diabetes, arteriosclerosis, obesity, various autoimmune diseases and cancer (e.g. colorectal, breast, ovarian, lung). or chromosomal abnormality (either prenatally or postnatally); or a predisposition to a disease or condition (e.g. obesity, artherosclerosis, cancer).

Depending on the biological sample, the diagnosis for a genetic disease, chromosomal aneuploidy or genetic predisposition can be preformed either pre- or postnatally.

Viruses (HIV,CMV), bacteria, fungi and other infectious organisms contain distinct nucleic acid sequences, which are different from the sequences contained in the host cell. Therefore, infectious organisms can also be detected and identified based on their specific DNA sequences.

Since the sequence of 17 nucleotides is specific on statistical grounds, relatively short nucleic acid sequences can be used to detect normal and defective genes in higher organisms and to detect infectious microorganisms (e.g. bacteria, fungi, protists and yeast) and viruses. DNA sequences can even serve as a fingerprint for detection of different individuals within the same species. (Thompson, J. S. and M. W. Thompson, eds., *Genetics in Medicine*, W. B. Saunders Co., Philadelphia, Pa. (1986).

One process for detecting a wildtype ($D^{wt}$) and/or a mutant ($D^{mut}$) sequence in a target (T) nucleic acid molecule is shown in FIG. 1C. A specific capture sequence (C) is attached to a solid support (A) via a spacer (S). In addition, the capture sequence is chosen to specifically interact with a complementary sequence on the target sequence (T), the target capure site (TCS) to be detected through hybridization. However, if the target detection site (TDS) includes a mutation, X, which increases or decreases the molecular weight, mutated can be distinguished from wildtype by mass spectrometry.

Preferably, the detector nucleic acid (D) is designed such that the mutation would be in the middle of the molecule and the flanking regions are short enough so that a stable hybrid would not be formed if the wildtype detector oligonucleotide ($D^{wt}$) is contacted with the mutated target detector sequence as a control. The mutation can also be detected if the mutated detector oligonucleotide ($D^{mut}$) with the matching base at the mutated position is used for hybridization. If a nucleic acid obtained from a biological sample is heterozygous for the particular sequence (i.e. contain both $D^{wt}$ and $D^{mut}$), both $D^{wt}$ and $D^{mut}$ will be bound to the appropriate strand and the mass difference allows both $D^{wt}$ and $D^{mut}$ to be detected simultaneously.

Figure 8:
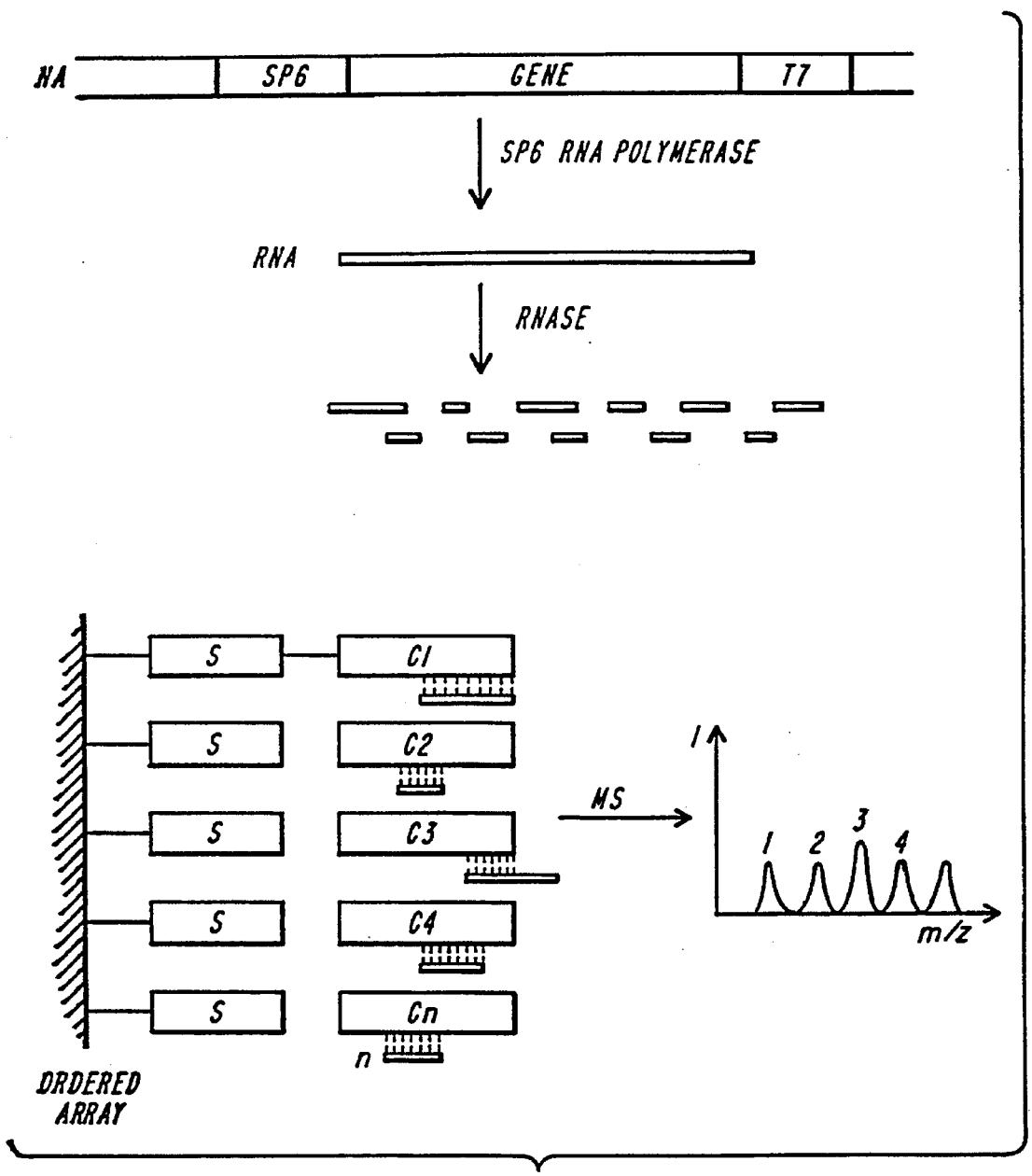
FIG. 8 is a diagram showing how RNA prepared as described in FIG. 7 can be specifically digested using one or more ribonucleases and the fragments captured on a solid support carrying the corresponding complementary sequences. Hybridization events and the actual molecular weights of the captured target sequences provide information on whether and where mutations in the gene are present. The array can be analyzed spot by spot using mass spectrometry. DNA can be similarly digested using a cocktail of nucleases including restriction endonucleases.

The process of this invention makes use of the known sequence information of the target sequence and known mutation sites. Although new mutations can also be detected. For example, as shown in FIG. 8, transcription of a nucleic acid molecule obtained from a biological sample can be specifically digested using one or more nucleases and the fragments captured on a solid support carrying the corresponding complementary nucleic acid sequences. Detection of hybridization and the molecular weights of the captured target sequences provide information on whether and where in a gene a mutation is present.

The present invention is further illustrated by the following examples which should not be construed as limiting in any way. The contents of all cited references (including literature references, issued patents, published patent applications, and co-pending patent applications) cited throughout this application are hereby expressly incorporated by reference.

EXAMPLE 1

Figure 9B:
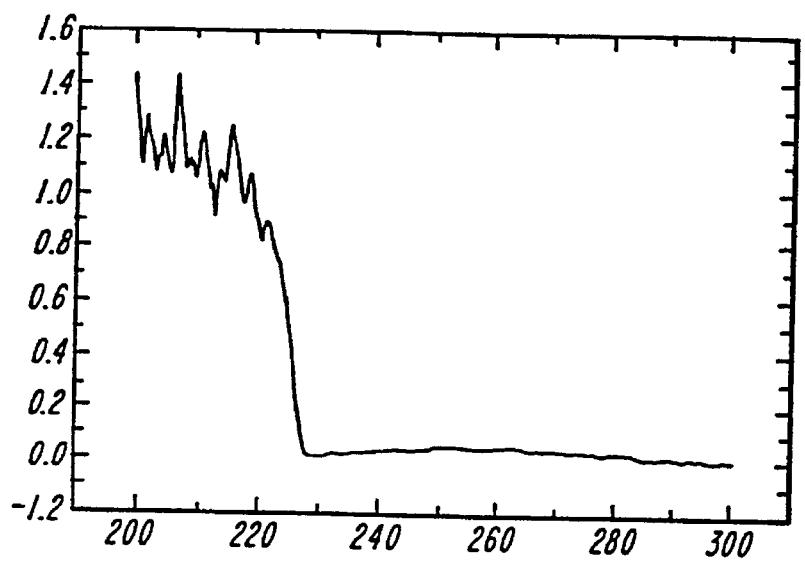
FIG. 9B shows a spectra resulting from the experiment described in the following Example 1 after three washing/centrifugation steps.
Figure 9C:
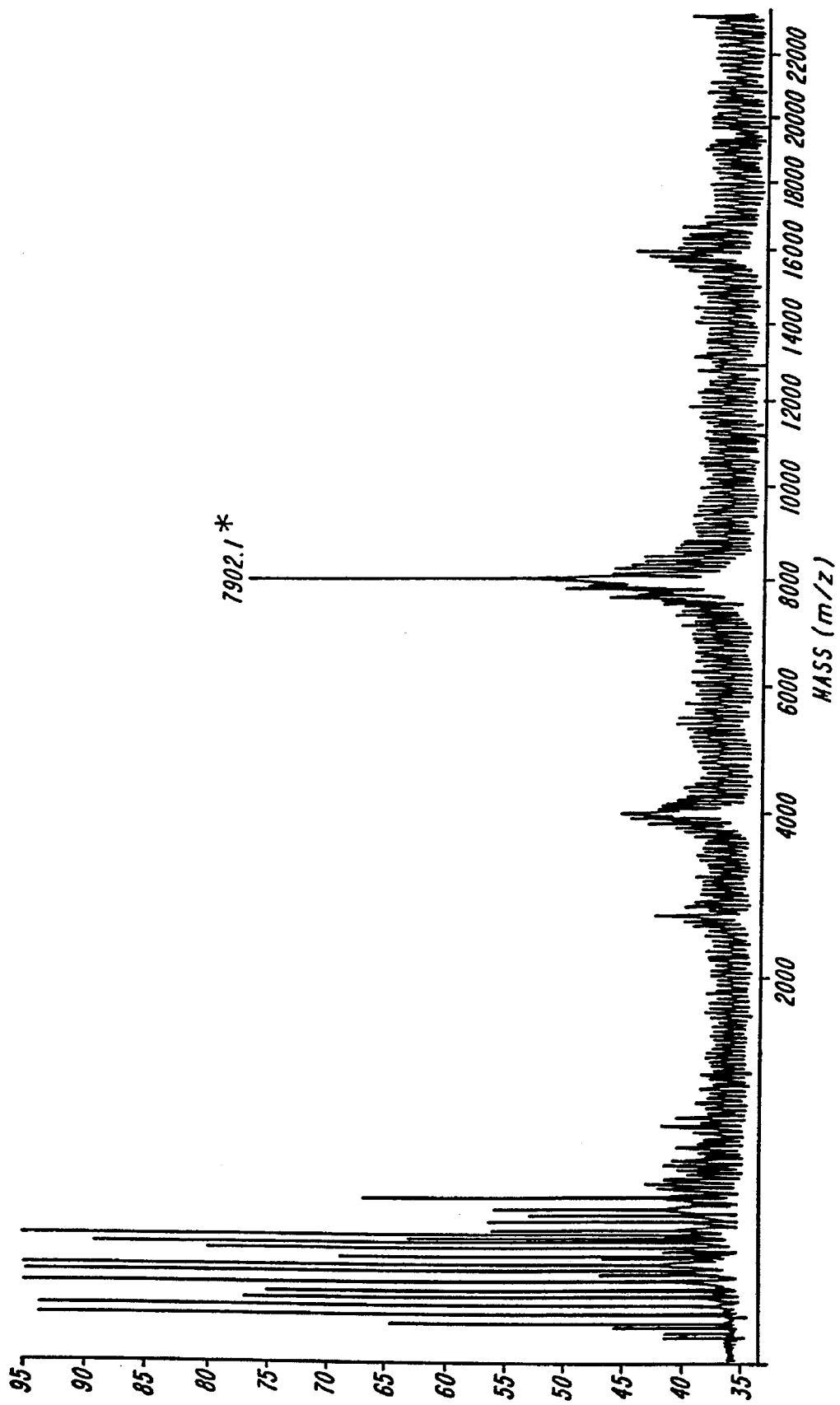
FIG. 9C shows a spectra resulting from the experiment described in the following Example 1 showing the successful desorption of the hybridized 26 mer off of beads.
Figure 10:
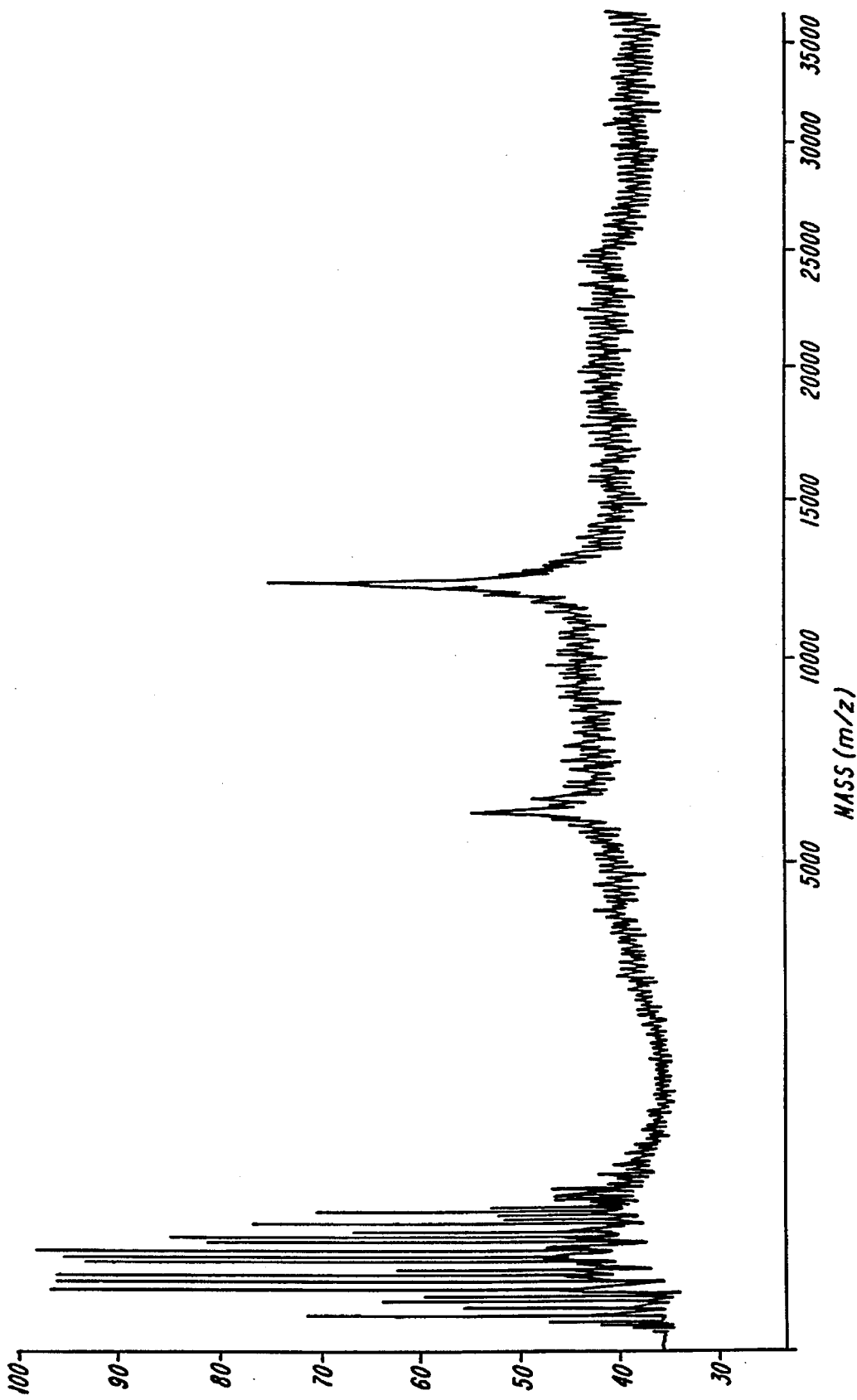
FIG. 10 shows a spectra resulting from the experiment described in the following Example 1 showing the successful desorption of the hybridized 46 mer. The efficiency of detection suggests that fragments much longer than 46 mers can also be desorbed.

MALDI-TOF desorption of oligonucleotides directly on solid supports 1 g CPG (Controlled Pore Glass) was functionalized with 3-(triethoxysilyl)epoxypropan to form OH-groups on the polymer surface. A standard oligonucleotide synthesis with 13 mg of the OH-CPG on a DNA synthesizer (Milligen, Model 7500) employing β-cyanoethyl-phosphoamidites (K öster et al., Nucleic Acids Res., 12, 4539 (1994)) and TAC N-protecting groups (Köster et al., Tetrahedron, 37, 362 (1981)) was performed to synthesize a 3'-$T_5$-50 mer oligonucleotide sequence in which 50 nucleotides are complementary to a "hypothetical" 50 mer sequence. $T_5$ serves as a spacer. Deprotection with saturated ammonia in methanol at room temperature for 2 hours furnished according to the determination of the DMT group CPG which contained about 10 umol 55 mer/g CPG. This 55 mer served as a template for hybridizations with a 26 mer (with 5'-DMT group) and a 46 mer (without DMT group). The reaction volume is 100 ul and contains about 1 nmol CPG bound 55 mer as template, an equimolar amount of oligonucleotide in solution (26 mer or 46 mer) in 20 mM Tris-HCI, pH 7.5, 10 mM $MgCl_2$ and 25 mM NaCl. The mixture was heated for 10' at 65° C. and cooled to 37° C. during 30' (annealing). The oligonucleotide which has not been hybridized to the polymer-bound template were removed by centrifugation and three subsequent washing/centrifugation steps with 100 ul each of ice-cold 50 mM ammoniumcitrate. The beads were air-dried and mixed with matrix solution (3-hydroxypicolinic acid/10 mM ammonium citrate in acetonitril/water, 1:1), and analyzed by MALDI-TOF mass spectrometry. The results are presented in FIGS. 9 and 10

EXAMPLE 2

Electrospray (ES) desorption and differentiation of an 18-mer and 19-mer

DNA fragments at a concentration of 50 pmole/ul in 2-propanol/10 mM ammoniumcarbonate (1/9, v/v) were analyzed simultaneously by an electrospray mass spectrometer.

Figure 11A:
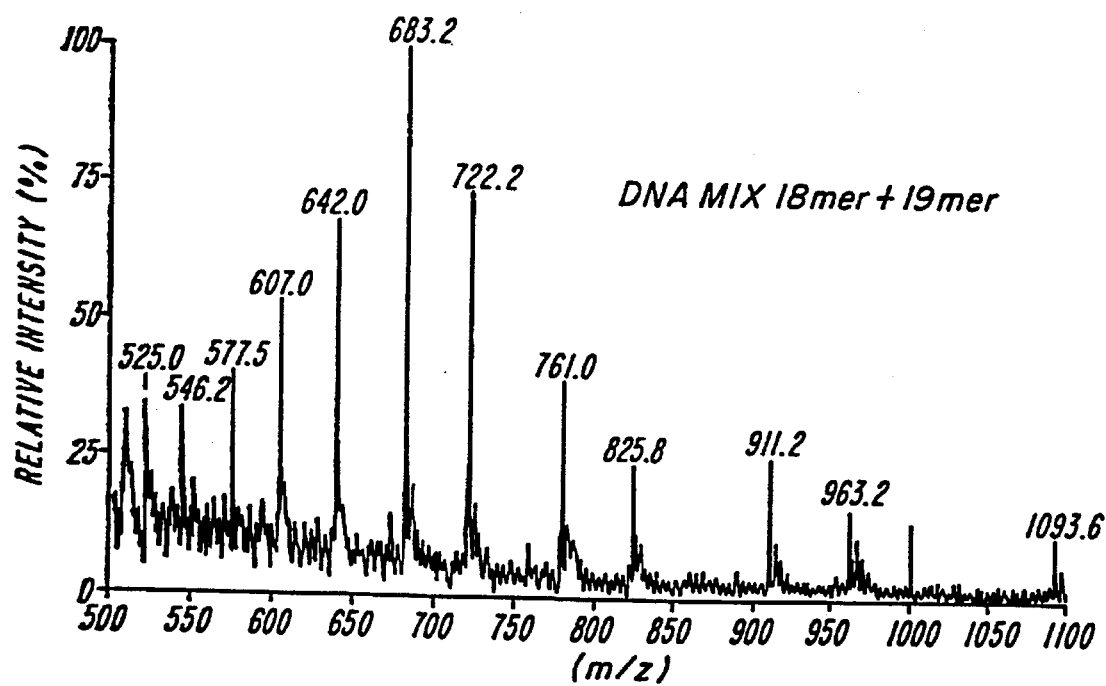
FIG. 11 shows a spectra resulting from the experiment described in the following Example 2 showing the successful desorption and differentiation of an 18-mer and 19-mer by electrospray mass spectrometry, the mixture (top), peaks resulting from 18-mer emphasized (middle) and peaks resulting from 19-mer emphasized (bottom)
Figure 11B:
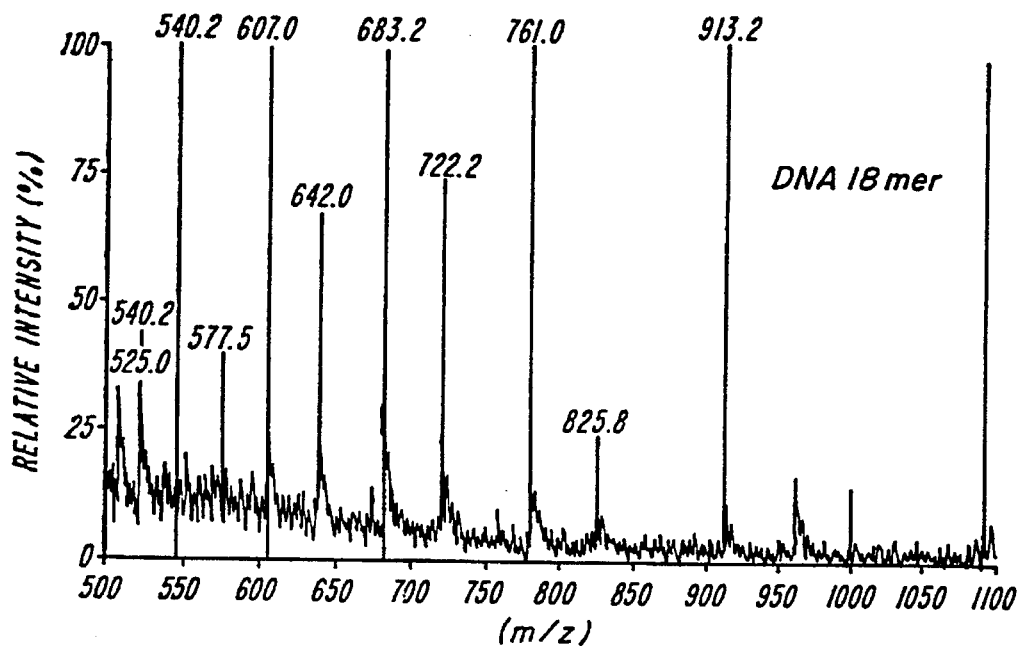
Figure 11C:
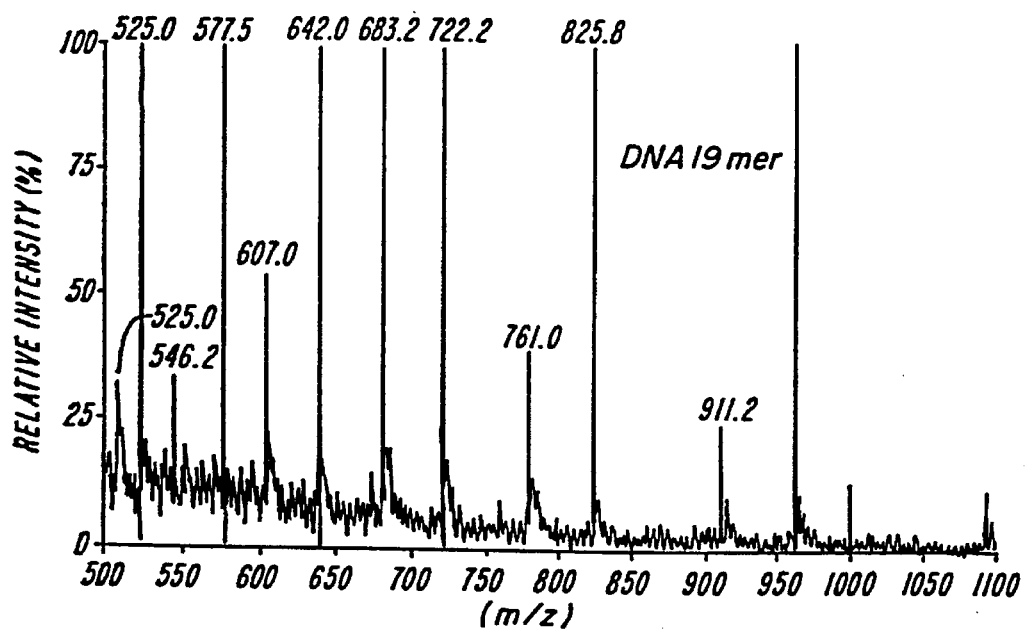

The successful desorption and differentiation of an 18-mer and 19-mer by electrospray mass spectrometry is shown in FIG. 11.

Equivalents

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. A process for detecting a target nucleic acid sequence present in a biological sample, comprising the steps of:
   a) obtaining a nucleic acid molecule containing a target nucleic acid sequence from a biological sample;
   b) hybridizing a detector oligonucleotide with the target nucleic acid sequence, wherein at least one of the detector oligonucleotide or the target nucleic acid sequence has been conditioned;
   c) removing unhybridized detector oligonucleotide;
   d) ionizing and volatizing the product of step c); and
   e) detecting the detector oligonucleotide by mass spectrometry, wherein detection of the detector oligonucleotide indicates the presence of the target nucleic acid sequence in the biological sample.

2. A process of claim 1 wherein prior to step b), the target nucleic acid sequence is immobilized onto a solid support to produce an immobilized target nucleic acid sequence.

3. A process of claim 2, wherein immobilization is accomplished by hybridization between a complementary capture nucleic acid molecule, which has been previously immobilized to a solid support, and a portion of the nucleic acid molecule, which is distinct from the target nucleic acid sequence.

4. A process of claim 2, wherein immobilization is accomplished via direct bonding between the solid support and a portion of the nucleic acid molecule, which is distinct from the target nucleic acid sequence.

5. A process of claim 2, wherein the solid support is selected from the group consisting of: beads, flat surfaces, pins and combs.

6. A process of claim 5, wherein immobilization is accomplished by hybridization between an array of complementary capture nucleic acid molecules, which have been previously immobilized to a solid support, and a portion of the nucleic acid molecule, which is distinct from the target nucleic acid sequence.

7. A process of claim 6, wherein the complementary capture nucleic acid molecules are oligonucleotides or oligonucleotide mimetics.

8. A process of claim 2, wherein the immobilization is reversible.

9. A process of claim 1, wherein prior to step c), the target nucleic acid sequence is amplified.

10. A process of claim 9, wherein the target nucleic acid sequence is amplified by an amplification procedure selected from the group consisting of: cloning, transcription, the polymerase chain reaction (PCR), the ligase chain reaction (LCR), and strand displacement amplification (SDA).

11. A process of claim 1 wherein the mass spectrometer is selected from the group consisting of: Matrix-Assisted Laser Desorption/Ionization Time-of-Flight (MALDI-TOF), Electrospray (ES), Ion Cyclotron Resonance (ICR), and Fourier Transform.

12. A process of claim 1, wherein the sample is conditioned by mass differentiating at least two detector oligonucleotides or oligonucleotide mimetics to detect and distinguish at least two target nucleic acid sequences simultaneously.

13. A process of claim 12, wherein the mass differentiation is achieved by differences in the length or sequence of the at least two oligonucleotides.

14. A process of claim 13, wherein the mass differentiation is acheived by the introduction of mass modifying functionalities in the base, sugar or phosphate moiety of the detector oligonucleotides.

15. A process of claim 12, wherein the mass differentiation is achieved by exchange of cations at the phosphodiester bond.

16. A process of claim 1, wherein the nucleic acid molecule obtained from a biological sample is amplified into DNA using mass modified dideoxynucleoside triphosphates and DNA dependent DNA polymerase prior to mass spectrometric detection.

17. A process of claim 1, wherein the nucleic acid molecule obtained from a biological sample is amplified into RNA using mass modified ribonucleoside triphosphates and DNA dependent RNA polymerase prior to mass spectrometric detection.

18. A process of claim 1 wherein the target nucleic acid sequence is indicative of a disease or condition selected from the group consisting of a genetic disease, a chromosomal abnormality, a genetic predisposition, a viral infection, a fungal infection and a bacterial infection.

19. A process for detecting a target nucleic acid sequence present in a biological sample, comprising the steps of:
   a) obtaining a nucleic acid molecule containing a target nucleic acid sequence from a biological sample;
   b) amplifying the target nucleic acid sequence, thereby obtaining an amplified target nucleic acid sequence;
   c) hybridizing a detector oligonucleotide with the amplified target nucleic acid sequence, wherein at least one of the detector oligonucleotide or the amplified target nucleic acid sequence has been conditioned;
   d) removing unhybridized detector oligonucleotide;
   e) ionizing and volatizing the product of step c); and
   f) detecting the detector oligonucleotide by mass spectrometry, wherein detection of the detector oligonucleotide indicates the presence of the target nucleic acid sequence in the biological sample.

20. A process of claim 19, wherein the target nucleic acid is amplified by an amplification procedure selected from the group consisting of: cloning, transcription, the polymerase chain reaction (PCR), the ligase chain reaction (LCR), and strand displacement amplification (SDA).

21. A process of claim 20, wherein the mass spectrometer is selected from the group consisting of: Matrix-Assisted Laser Desorption/Ionization, Time-of-Flight (MALDI-TOF), Electrospray (ES), Ion Cyclotron Resonance (ICR), and Fourier Transform.

22. A process of claim 19, wherein the sample is conditioned by mass differentiation.

23. A process of claim 22, wherein the mass differentiation is achieved by mass modifying functionalities attached to primers used for amplifications.

24. A process of claim 22, wherein the mass differentiation is achieved by exchange of cations at the phosphodiester bond.

25. A process of claim 22, wherein the mass differentiation is achieved by introduction of a mass modifying functionality into a base, sugar or phosphate moiety of an amplified nucleic acid molecule.

26. A process of claim 19, wherein the nucleic acid molecule is DNA.

27. A process of claim 19, wherein the nucleic acid molecule is RNA.

28. A process of claim 19, wherein prior to step c) amplified target nucleic acid sequences are immobilized onto a solid support to produce immobilized target nucleic acid sequences.

29. A process of claim 28, wherein immobilization is accomplished by hybridization between a complementary capture nucleic acid molecule, which has been previously immobilized to a solid support, and the target nucleic acid sequence.

30. A process of claim 28, wherein the solid support is selected from the group consisting of: beads, flat surfaces, pins and combs.

31. A process of claim 28, wherein the immobilization is reversible.

32. A process of claim 19 wherein the target nucleic acid sequence is indicative of a disease or condition selected from the group consisting of a genetic disease, a chromosomal abnormality, a genetic predisposition, a viral infection, a fungal infection and a bacterial infection.

33. A process for detecting a target nucleic acid sequence present in a biological sample, comprising the steps of:
   a) obtaining a target nucleic acid sequence from a biological sample;
   b) amplifying and conditioning the target nucleic acid sequence, thereby producing amplified and conditioned nucleic acid molecules;
   c) digesting the amplified and conditioned nucleic acid molecules using at least one appropriate nucleases, thereby producing conditioned fragments;
   d) ionizing and volatizing the conditioned fragments; and
   e) detecting the conditioned fragments to determine the presence of the target nucleic acid sequence.

34. A process of claim 33, wherein prior to step d), amplified target nucleic acid sequences are immobilized onto a solid support to produce immobilized target nucleic acid sequences.

35. A process of claim 34, wherein immobilization is accomplished by hybridization between an array of complementary capture nucleic acid molecules, which have been previously immobilized to a solid support, and a portion of the nucleic acid molecule, which is distinct from the target nucleic acid sequence.

36. A process of claim 34, wherein the solid support is selected from the group consisting of: beads, flat surfaces, pins and combs.

37. A process of claim 34, wherein the complementary capture nucleic acid sequences are oligonucleotides or oligonucleotide mimetics.

38. A process of claim 34, wherein the immobilization is reversible.

39. A process of claim 33 wherein the mass spectrometer is selected from the group consisting of: Matrix-Assisted Laser Desorption/Ionization Time-of-Flight (MALDI-TOF), Electrospray (ES), Ion Cyclotron Resonance (ICR), and Fourier Transform.

40. A process of claim 33, wherein the amplified nucleic acid molecules are conditioned by mass differentiation.

41. A process of claim 40, wherein the mass differentiation is achieved by exchange of cations at the phosphodiester bond.

42. A process of claim 33, wherein the mass differentiation is achieved by the introduction of mass modifying functionalities in the base, sugar or phosphate moiety of an amplified nucleic acid molecules.

43. A process of claim 33, wherein step a), the target nucleic acid sequence is amplified into DNA using mass modified dideoxynucleoside triphosphates and DNA dependent DNA polymerase.

44. A process of claim 33, wherein step a), the target nucleic acid sequence is amplified into RNA using mass modified ribonucleoside triphosphates and DNA dependent RNA polymerase.

45. A process of claim 33 wherein the target nucleic acid sequence is indicative of a disease or condition selected from the group consisting of a genetic disease, a chromosomal abnormality, a genetic predisposition, a viral infection, a fungal infection and a bacterial infection.

* * * * *

UNITED STATES PATENT AND TRADEMARK OFFICE
CERTIFICATE OF CORRECTION

PATENT NO. : 5,605,798
DATED : February 25, 1997
INVENTOR(S) : Köster, H.

It is certified that error appears in the above-identified patent and that said Letters Patent is hereby corrected as shown below:

IN THE CLAIMS:

Please replace claims 16 with the following claim:

16. A process of claim 1, wherein the nucleic acid molecule obtained from a biological sample is amplified into DNA using mass modified deoxynucleoside triphosphates and DNA dependent DNA polymerase prior to mass spectrometric detection.

Signed and Sealed this

Thirty-first Day of July, 2001

Attest:

NICHOLAS P. GODICI
Attesting Officer      Acting Director of the United States Patent and Trademark Office